(12) United States Patent
Legarda Ibañez

(10) Patent No.: US 7,186,711 B2
(45) Date of Patent: Mar. 6, 2007

(54) FLUMAZENIL FOR THE TREATMENT OF COCAINE DEPENDENCY

(75) Inventor: Juan Jose Legarda Ibañez, Madrid (ES)

(73) Assignee: Hythiam, Inc., Los Angeles, CA (US)

( * ) Notice: Subject to any disclaimer, the term of this patent is extended or adjusted under 35 U.S.C. 154(b) by 425 days.

(21) Appl. No.: 10/622,068

(22) Filed: Jul. 15, 2003

(65) Prior Publication Data
US 2006/0122219 A1    Jun. 8, 2006

(51) Int. Cl.
A61K 31/55    (2006.01)

(52) U.S. Cl. .................................. 514/218; 514/220
(58) Field of Classification Search ............... 514/218, 514/220
See application file for complete search history.

(56) References Cited

U.S. PATENT DOCUMENTS

| | | | | |
|---|---|---|---|---|
| 5,028,611 | A * | 7/1991 | Halikas | 514/277 |
| 5,229,120 | A * | 7/1993 | DeVincent | 424/725.1 |
| 6,346,528 | B1 * | 2/2002 | Yelle | 514/220 |
| 6,451,783 | B1 * | 9/2002 | Hadcock et al. | 514/183 |
| 6,455,276 | B1 | 9/2002 | Le Bourdelles et al. | |
| 6,740,677 | B2 | 5/2004 | Xue et al. | |

OTHER PUBLICATIONS

Gasior et al. Chlormethiazole: Effectiveness against Toxic Effects of Cocaine in Mice. The Journal of Pharmacology and Experimental Therapeutics. vol. 295, No. 1, pp. 153-161. Oct. 2000.*
Derlet, R.W. et al., Anticonvulsivant Modification of Cocaine-Induced Toxicity in the Rat, Neuropharmacology, 1990, vol. 29, No. 3, pp. 255-259.
Derlet, R.W. et al., Flumazenil Induces Seizures and Death in Mixed Cocaine-Diazepam Intoxications, Annals of Emergency Medicine, 1994, vol. 23, No. 3, pp. 494-498.
Malbrain, M.L. et al., A Massive, Near-Fatal Cocain Intoxication in a Body-Stuffer, Acta Clinica, Belgium, 1994, vol. 49, No. 1, pp. 12-18.
Uki, F. et al., The Effect of Flumazenil Administration on Acute Cocaine Intoxication of Rats, Arukoru Kenkyu to Yakubutzu Izon, 1994, vol. 29, No. 2, pp. 92-102.
Woolf, A., Cocaine Poisoning, Clinical Toxicology Review, May 1995, Vo. 18, No. 8.
Baldwin, H.A., et al., "Flumazenil Prevents the Development of Chlordiazepoxide Withdrawal in Rats Tested in the Social Interaction Test of Anxiety," Psychopharmacology, vol. 97, No. 3, pp. 424-426 (1989) (Abstract Only).
Brooks-Kayal-A.R., et al., "Human Neuronal γ-Aminobutyric Acid$_A$ Receptors: Coordinated Subunit mRNA Expression and Functional Correlates in Individual Dentate Granule Cells," J. Neuroscience, vol. 19, No. 19, pp. 8312-8318 (1999).
Criswell, H.E., et al., "Effect of Zolpidem on Gamma-aminobutyric Acid (GABA)-Induced Inhibition Predicts the Interaction of Ethanol with GABA on Individual Neurons in Several Rat Brain Regions," J. Pharmacol. Exp. Therp., vol. 273, No. 1, pp. 526-536 (1995) (Abstract Only).
Ferrara, G., et al., "Increased Expression of the Neuropeptide Y receptor Y1 Gene in the Medical Amygdala of Transgenic Mice Induced by Long-term Treatment with Progesterone or Allopregnanolone," J. Neurochemistry, vol. 79, pp. 417-425 (2001).
Frostholm, A., et al., "Harmaline-induced Changes in Gamma Aminobutyric Acid$_A$ Receptor Subunit mRNA Expression in Murine Olivocerebellar Nuclei," Molecular Brain Research, vol. 85, pp. 200-208 (2000).
Gee, K., et al., "A Putative Receptor for Neurosteroids on the GABA$_A$ Receptor Complex: The Pharmacological Properites and Therapeutic Potential of Epalons," Crit. Rev. Neurobiol, vol. 9, Nos. 2-3, pp. 207-227 (1995).
Gulinello, M., et al., "Progesterone Withdrawal Increases the α4 Subunit of the GABA$_A$ Receptor in Male Rats in Association With Anxiety and Altered Pharmacology—A Comparison With Female Rats," Neuropharmacology, vol. 43, pp. 701-714 (2000).
Gulinello, M., et al., "Anxiogenic Effects of Neurosteroid Exposure: Sex Differences and Altered GABA$_A$ Receptor Pharmacology in Adult Rats," J. Pharmacology and Experimental Therapeutics, vol. 305, No. 2, pp. 541-548 (2003).
Hawkinson, J.E., "Substituted 3β-Phenylethynyl Derivatives of 3α-Hydroxy-5α-pregnan-20-one: Remarkably Potent Neuroactive Steroid Modulators of γ-Aminobutyric Acid$_A$ Receptors," J. Pharmacology and Experimental Therapeutics, vol. 287, No. 1, p. 198-207 (1998).
Hogenkamp, D.J., et al., "Synthesis and in Vitro Activity of 3β-Substituted-3α-Hydroxypregnan-20-ones: Allosteric Modulators of the GABA$_A$ Receptor," J. Med. Chem., vol. 40, pp. 61-72 (1996).
Hsu, F., et al., "Progesterone Withdrawal Reduces Paired-Pulse Inhibition in Rate Hippocuampus: Dependence on GABA$_A$ Receptor α4 Subunit Upregulation," J. Neurophysiol., vol. 89, pp. 186-198 (2003).
Krogsgaard-Larsen, P., et al., "GABA$_A$ Agonists and Partial Agonists: THIP (Gaboxadol) as a Non-Opioid Analgesic and a Novel Type of Hypnotic," Biochemical Pharmacology, vol. 68, pp. 1573-1580 (2004).
Holt, R.A., et al., "Chronic Treatment with Diazepam or Abecarnil Differently Affects the Expression of GABA$_A$ Receptor Subunit mRNAs in the Rat Cortex," Neuropharmacology, vol. 35, Nos. 9 & 10, pp. 1457-1463 (1996); Abstract only.
Lan, N.C., et al., "Differential Responses of Expressed Recombinant Human Gamma-aminobutyric acid$_A$ Receptors to Neurosteroids," J. Neurochem., vol. 57, No. 5, pp. 1818-1821 (1991) (Abstract Only).

(Continued)

Primary Examiner—Sreenivasan Padmanabhan
Assistant Examiner—Jennifer Kim
(74) Attorney, Agent, or Firm—Kilpatrick Stockton LLP

(57) ABSTRACT

The invention relates to the use of flumazenil to produce a medicament for the treatment of cocaine dependency. The flumazenil can be administered sequentially in small quantities at short intervals until a therapeutically effective quantity for the treatment of cocaine dependency has been administered.

18 Claims, No Drawings

OTHER PUBLICATIONS

Lee, C., et al., "Effects of Benzodiazepine Receptor Antagonist, Flumazenil, on Antinociceptive and Behavioural Responses to the Elevated Plusmaze in Mice," *Neuropharmacology*, vol. 30, No. 12A, pp. 1263-1267 (1991) (Abstract Only).

Medina, J.H., et al., "Overview-Flavonoids: A New Family of Benzodiazepine Receptor Ligands," *Neurochemical Research*, vol. 22, No. 4, pp. 419-425 (1997).

Smith, S.S., et al., "Neurosteroid Administration and Withdrawal Alter $GABA_A$ Receptor Kinetics in CA1 Hippocampus of Female Rats," *J. Physiol.*, vol. 567, Pt. 2. pp. 421-436 (2005) (Abstract Only).

Sur, C., et al., "Preferential Coassembly of $\alpha 4$ and $\delta$ Subunits of the $\gamma$-Aminobutyric Acid$_A$ Receptor in Rat Thalamus," *American Society of Pharmacology and Experimental Therapeutics*, vol. 56, pp. 110-115 (1998).

Van Miert, A.S., et al., "Appetite-modulating Drugs in Dwarf Goats, With Special Emphasis on Benzodiazepine-induced Hyperphagia and Its Antagonism by Flumazenil and RO 15-3505," *J. Vet. Pharmacol.Ther.*, vol. 12, No. 2, pp. 147-156 (1989); Abstract only.

Whittemore, E.R., et al., "Pharmacology of the Human Gamma-aminobutyric acid$_A$ Receptor Alpha 4 Subunit Expressed in *Xenopus laevis* Oocytes," *Mol. Pharmacol.*, vol. 50, No. 5, pp. 1364-1375 (1996) (Abstract Only).

Wisden, W., et al., "Cloning, Pharmacological Characteristics and Expression Pattern of the Rat $GABA_A$ Receptor Alpha 4 Subunit," *FEBS Lett.*, vol. 289, No. 2, pp. 227-230 (1991) (Abstract Only).

Adkins, C.E., et al., "$\alpha 4\beta 3\delta$ $GABA_A$ Receptors Characterized by Fluorescence Resonance Energy Transfer-derived Measurements of Membrane Potential," *J. Biological Chemistry*, vol. 276, No. 42, pp. 38934-38939 (2001).

Akk, G., et al., "Activation of GABA(A) Receptors Containing the alpha4 subunit by GABA and Pentobarbital," *J. Physiol.*, vol. 556, Part 2, , pp. 387-399 (2004).

Banerjee, P.K., et al., "Alterations in $GABA_A$ Receptor $\alpha 1$ and $\alpha 4$ Subunit mRNA Levels in Thalamic Relay Nuclei Following Absence-like Seizures in Rats," *Experimental Neurology*, vol. 154, pp. 213-223 (1998).

Biggio, G., et al., "$GABA_A$-receptor Plasticity During Long-Term Exposure to and Withdrawal from Progesterone," *Int. Rev. Neurobiol.*, vol. 46, pp. 207-241 (2001); Abstract only.

Burt, D.R., "Alpha Subunit Position and GABA Receptor Function," *Science's STKE*, No. 270, PE5, pp. 1-2 (2005).

Lovick, T.A., et al., "Changes in $GABA_A$ Receptor Subunit Expression in the Midbrain During the Oestrous Cycle in Wistar Rats," *Neuroscience*, vol. 131, pp. 397-405 (2005).

Lujan, R., et al., "Glutamate and GABA Receptor Signalling in the Developing Brain," *Neuroscience* , vol. 130, pp. 567-580 (2005).

Mody, I., "Distinguishing between $GABA_A$ Receptors Responsible for Tonic and Phasic Conductances," *Neurochemical Research*, vol. 26, Nos. 8-9, pp. 907-913 (2001).

Porter, B.E., et al., "Heterogenous GABA(A) Receptor Subunit Expression in Pediatric Epilepsy Patients," *Neurobiol. Dis.*, vol. 18, No. 3, pp. 484-491 (2005) (Abstract Only).

Quirk, G.J., et al., "Inhibition of the Amygdala: Key to Pathological States?," *Ann. N.Y. Acad. Sci.*, vol. 985, pp. 263-272 (2003).

Rissman, R.A., et al., "Subregional Analysis of $GABA_A$ Receptor Subunit mRNAs in the Hippocampus of Older Persons with and without Cognitive Impairment," *J. Chemical Neuroanatomy*, vol. 28, pp. 17-25 (2004).

Saitoh, K., et al., "Nigral GABAergic Inhibition Upon Mesencephalic Dopaminergic Cell Groups in Rats," *Eur. J. Neurosci.*, vol. 19, No. 9, pp. 2399-2409 (2004) (Abstract Only).

Sedvall, G., et al., "Recent Advances in Psychiatric Brain Imaging," *Acta Radiol.Suppl.*, vol. 374, pp. 113-115 (1990) (Abstract Only).

Smith, A.J., et al., "Effect of a Subunit on Allosteric Modulation of Ion Channel Function in Stably Expressed Human Recombinant $\gamma$-Aminobutyric Acid$_A$ Receptors Determined Using $^{36}Cl$ Ion Flux," *Molecular Pharmacology*, vol. 59, No. 5, pp. 1108-1118 (2001).

Smith, S.S., et al., "$GABA_A$ Receptor $\alpha 4$ Subunit Suppression Prevents Withdrawal Properties of an Endogenous Steroid," *Nature*, vol. 392, pp. 926-930 (1998).

Weinbroum, A.A., et al., "Flumazenil Potentiation of Postoperative Morphine Analgesia," *Clin J. Pain*, vol. 16, No. 3, pp. 193-199 (2000) (Abstract Only).

White, J.A., et al., "Antagonism of a Nicotine Plus Midazolam Discriminative Cue in Rats," *Behav. Pharmacol.*, vol. 5, No. 3, pp. 361-355 (1994) (Abstract Only).

Yang, W., "Cloning and Characterization of the Human $GABA_A$ Receptor Alpha 4 Subunit: Identification of a Unique Diazepam-Insensitive Binding Site," *Eur. J. Pharmacol.*, vol. 291, No. 3, pp. 319-325 (1995) (Abstract Only).

Zheng, T.M., et al., "Chronic Flumazenil Alters $GABA_A$ Receptor Subunit mRNA Expression, Translation Product Assembly and Channel Function in Neuronal Cultures," *J. Pharmacol. Exp. Ther.*, vol. 277, No. 1, pp. 525-533 (1996) (Abstract Only).

Zheng, T.M., et al., "Changes in $\gamma$-aminobutyrate Type A Receptor Subunit mRNAs, Translation Product Expression, and Receptor Function During Neuronal Maturation in vitro," *Proc. Natl. Acad. Sci. USA*, vol. 91, pp. 10952-10956 (1994).

* cited by examiner

FLUMAZENIL FOR THE TREATMENT OF COCAINE DEPENDENCY

FIELD OF THE INVENTION

The invention relates to the use of pharmaceutical compositions that contain flumazenil in the treatment of cocaine dependency.

BACKGROUND OF THE INVENTION

Cocaine is a drug with a powerful stimulating effect that increases alertness (reduces fatigue), increases concentration, reduces appetite, increases physical resistance, and may induce a state of well being or euphoria.

Cocaine may be taken orally, inhaled nasally in powdered form, or injected, usually, directly in a vein. When heated with sodium bicarbonate, it is converted into a base called crack, which may be smoked.

Cocaine increases the blood pressure and the heart rate and may cause a fatal heart attack Other effects include gastrointestinal disorders, intestinal damage, intense nervousness, a sensation that something is moving under the skin, epileptic attacks, hallucinations, sleep disorders, paranoid delirium, and violent behavior.

Due to the fact that the effects of cocaine are of short duration, ca. 30 minutes, cocaine users usually take repeated doses of the drug. To reduce some of the extreme nervousness caused by cocaine, many addicts use heroin or nervous system depressants, for example, alcohol.

Cocaine withdrawal syndrome is a syndrome which develops in cocaine addicts who stop using cocaine. The reactions typical of this syndrome include extreme fatigue and depression, i.e., reactions opposite the effects of the drug, and, frequently, suicidal tendencies appear upon discontinuation of use of the drug.

Cocaine dependency is usually treated, initially, by a psychosocial treatment. However, patients or individuals with severe forms of cocaine dependency that do not respond to said psychosocial treatment may be subjected to a pharmacological treatment. Currently, no truly effective treatment is available for cocaine withdrawal syndrome.

A review of the various pharmacological treatments to reduce the symptoms of cocaine dependency and to combat cocaine withdrawal syndrome can be found in "Practice Guideline for the Treatment of Patients With Substance Use Disorders: Alcohol, Cocaine and Opioids", produced by the Work Group On Substance Use Disorders of the American Psychiatric Association and published in Am. J. Psychiatry 152:11, Nov. 1995 Supplement, pp. 36–39.

This publication states that approximately 20 different pharmaceutical products have been studied for the purpose of finding an effective pharmacological treatment for cocaine dependency, although there is still no truly effective treatment available. The most promising results seem to have been obtained with desipramine and amantadine although there are studies that could not confirm the positive expectations created, possibly due to differences in the cocaine addict population and the route of administration of the drug. Other pharmaceuticals tested have been carbamazepine, pergolide, carbidopalL-dopa, fluoxetine, flupenthixol, bupropion, maprolitine, phenelzine, buprenorphine, and methadone.

Likewise, the above referenced publication states that treatment with dopamine agonists, for example, amantadine, reduces the symptoms of cocaine withdrawal syndrome, although two later studies could not confirm these results.

Initial studies with bromocriptine yielded some results in the treatment of cocaine withdrawal syndrome that were also not subsequently confirmed. In fact, Moscoviz et al., J. Gen. Intern. Med. 1993, 8:1–4, did not find a significant reduction between bromocriptine and placebo in outpatients.

In none of the reviews mentioned is the use of flumazenil considered in the treatment of cocaine dependency.

Flumazenil[ethyl8-fluoro-5,6-dihydro-5-methyl-6-oxo-4H-imidazol[1,5-a][1,4]benzodiazepine-3-carboxylate] is a benzodiazepine antagonist which selectively blocks the effects exerted on the central nervous system via the benzodiazepine receptors. This active principle is indicated to neutralize the central sedative effect of the benzodiazepines; consequently, it is regularly used in anesthesia to end the general anesthesia induced and maintained with benzodiazepines in hospitalized patients, or to stop the sedation produced with benzodiazepines in patients undergoing brief diagnostic or therapeutic procedures on an inpatient or outpatient basis.

BRIEF DESCRIPTION OF THE INVENTION

The invention deals with the problem of developing a method for the treatment of cocaine dependency.

The solution provided by this invention is based on the use of flumazenil in the treatment of cocaine dependency.

Thus, one object of this invention consists in the use of flumazenil to reduce or eradicate the symptoms of cocaine dependency.

An additional object of this invention consists in the use of flumazenil to produce a medicament for the treatment of cocaine dependency.

Another additional object of this invention consists in a method for the treatment of cocaine dependency that includes administration of a therapeutically effective quantity of flumazenil to a patient in need of said treatment.

DETAILED DESCRIPTION OF THE INVENTION

The invention relates to the use of flumazenil in the production of a medicament for the treatment of cocaine dependency. In the sense used in this description, the term "cocaine dependency" includes cocaine abuse, cocaine withdrawal syndrome, and relapse.

In one embodiment, flumazenil is administered sequentially, at short time intervals, in small quantities, until a therapeutically effective quantity for the treatment of cocaine dependency has been administered.

More specifically, the invention relates to the use of flumazenil to produce a medicament for sequential administration, at time intervals between 1 and 15 minutes, of quantities of flumazenil between 0.1 and 0.3 mg, until a therapeutically effective quantity, usually between 1.5 and 2.5 mg/day, of flumazenil to treat cocaine dependency has been administered.

Although the therapeutically effective daily dose of flumazenil could be administered in a single administration, it was discovered, surprisingly, that flumazenil can be safely administered to patients with cocaine dependency, in small quantities, applied sequentially and separated by a relatively short interval of time, until a therapeutically effective quantity of flumazenil to treat cocaine dependency is reached. This surprising discovery means that it is possible to administer flumazenil in small successive doses to treat cocaine dependency in a very short period of time, which reduces the risk of secondary effects in the patient and provides a better use of flumazenil to treat the symptoms of cocaine dependency.

Example 1 demonstrates that the administration to patients of 2 mg/day of flumazenil divided into doses of 0.2 mg every 3 minutes eradicates the symptoms of cocaine dependency in a high percentage of the patients treated.

Consequently, in a specific embodiment, the invention relates to the use of flumazenil to produce a medicament for administration, sequentially, at intervals of 3 minutes, of 0.2 mg of flumazenil, until a therapeutically effective quantity of 2 mg/day of flumazenil has been administered, to treat cocaine dependency.

Flumazenil may be administered by any appropriate route of administration, for example, orally or parenterally, for which it will be formulated with the appropriate excipients for the form of administration to be used. In one embodiment, flumazenil is administered by IV.

The invention also relates to a method for the treatment of cocaine dependency that includes the administration to a patient in need of said treatment of a therapeutically effective quantity of flumazenil, usually between 1.5 and 2.5 mg/day of flumazenil.

In one embodiment, the method for the treatment of cocaine dependency provided by this invention includes the administration to a patient in need of said treatment of a therapeutically effective quantity of flumazenil, usually between 1.5 and 2.5 mg/day of flumazenil, broken down into quantities of flumazenil between 0.1 and 0.3 mg and intended for sequential administration, at intervals of time between 1 and 15 minutes, until said therapeutically effective quantity of flumazenil to treat cocaine dependency is reached.

In a specific embodiment, the invention provides a method for the treatment of cocaine dependency that includes the administration to a patient in need of said treatment of 2 mg/day of flumazenil, broken down into quantities of 0.2 mg of flumazenil intended for sequential administration every 3 minutes until said quantity of 2 mg/day of flumazenil is reached.

The method for the treatment of cocaine dependency provided by this invention is applicable to any patient who, when the treatment is to begin, has no acute or uncompensated illness, or is not taking medication contraindicated with flumazenil. In general, the method of treatment of cocaine dependency provided by this invention begins with a complete medical and psychological examination. Normally, before and after administration of flumazenil, the symptoms of cocaine withdrawal, heart rate, and blood pressure are evaluated. If the patient presents an anxiety crisis, it is possible to administer an appropriate therapeutic agent, for example, clomethiazole, before administration of flumazenil. Likewise, if the patient presents a significant disphoric reaction, the first administration of flumazenil is carried out under sedation, for example, with propofol, under intensive care conditions. The administration of flumazenil may be carried out orally or intravenously, for example, by boluses that contain the appropriate quantity and under observation of the patient's reaction. Once inpatient treatment has concluded, as part of the therapeutic program, the patient must continue pharmacological treatment and, optionally, continue sessions with his therapist to evaluate his progress.

The following example demonstrates the invention and must not be considered to limit the scope thereof.

EXAMPLE 1

Treatment of Patients with Flumazenil Sequentially and at Low Dose 1.1 Experimental Protocol 3 cocaine addicts (2 men and 1 woman) voluntarily entered a treatment program to discontinue the use of cocaine. Said patients were provided the appropriate information and the corresponding informed consent form was obtained from them. The patients were warned not to use cocaine the morning on which the treatment was to be carried out to enable better evaluation of the withdrawal symptoms.

Table 1 summarizes the characteristics of the patients treated associated with cocaine use.

TABLE 1

Characteristics of the patients associated with cocaine use

| | Patient code | |
|---|---|---|
| Age (years) | P01 | 27 |
| | P02 | 31 |
| | P03 | 35 |
| Age at the beginning of daily cocaine use (years) | P01 | 25 |
| | P02 | 30 |
| | P03 | 33 |
| Quantity used in mg during the last 30 days prior to treatment | P01 | 6,000 |
| | P02 | 5,000 |
| | P03 | 500 |
| Number of previous detoxifications | P01 | 0 |
| | P02 | 0 |
| | P03 | 0 |

Before starting the treatment, the patients underwent a complete medical and psychological examination. The monitoring of the patients throughout the morning included exhaustive blood analysis with a complete count of all series (red, white and platelets), a biochemical profile [creatinine, glucose, urea, cholesterol (HDL and LDL), triglycerides, alkaline phosphatase, LDH (lactic dehydrogenase) and total proteins), hepatic function tests [GOT, GPT, GGT, bilirubin), electrocardiogram and, if need be, pregnancy test and x-ray examination. The exclusion criteria included acute or uncompensated illnesses. No patient was excluded after the pre-admission interview and the tests performed.

Before and after the administration of flumazenil the withdrawal symptomatology was evaluated using clinical criteria as well as heart rate and blood pressure.

Table 2 presents the treatment protocol followed during hospitalization.

TABLE 2

Protocol followed during hospitalization

| Time | Day of admission | Day 2 | Day of discharge |
|---|---|---|---|
| 9:00 am. | | Clomethiazole 192 mg Vitamin B Complex Piracetam 3 g (oral) Drink with vitamins, minerals, proteins, and amino acids | Clomethiazole 192 mg Vitamin B Complex Piracetam 3 g (oral) Drink with vitamins, minerals, proteins, and amino acids |
| 11:00 a.m. | | Flumazenil 2 mg | |

TABLE 2-continued

Protocol followed during hospitalization

| Time | Day of admission | Day 2 | Day of discharge |
|---|---|---|---|
| 1:00 p.m. | Clomethiazole 192 mg Vitamin B Complex Piracetam 3 g (oral) | | |
| 4:30 p.m. | Flumazenil 2 mg | | |
| 7:30 p.m. | Vitamin B Complex | Vitamin B Complex Disulfiram 250 mg | |
| 9:30 p.m. | Clomethiazole 384 mg | Clomethiazole 384 mg | |

Flumazenil was administered at a dose of 0.2 mg every 3 minutes (up to a total of 2 mg/day), because of the fact that the effects of flumazenil can be detected after 1–2 minutes after their administration. This quantity per dose was established to minimize the adverse side effects associated with withdrawal or interactions with other pharmaceuticals or psychopathologies. By administration of 2 mg of flumazenil in a period of time less than 1 hour, more than 55% of the GABA B receptors were occupied.

Patients who presented marked anxiety were administered an additional dose of 192 mg of clomethiazole 30 minutes before administration of flumazenil. Before beginning the initial administration of flumazenil, a test was performed consisting of the administration of a bolus of 0.1 mg of flumazenil to evaluate the subject's reaction. In those patients who had a significant disphoric reaction, the initial administration of flumazenil was performed under sedation with propofol under intensive care conditions.

Before discharge from the hospital, the following medications were prescribed:

Vitamin B complex: 1 month 1-1-0 (breakfast-lunch-dinner);

Piracetam 3 g: 1 week 1-0-0; piracetam 800 mg: 1 month 1-1-0;

Fluoxetine 20 mg: 2 months 1-0-0; and

Clomethiazole 192 mg: 1 week 1-0-1, and reduction to 0-0-0 during the second week.

1.2 Results

Of the 3 patients treated, in 2 cases the initial test was positive and the first administration of flumazenil was carried out under sedation with propofol in the intensive care unit.

Results after the First Administration of Flumazenil

The withdrawal symptomatology of the patients revealed that it was not possible to find a single physical or psychological symptom in any of the 3 patients.

The heart rate values of the patients, normal at the beginning [67±5 beats per minute (b.p.m.)], remained stable during the entire administration of flumazenil, with the exception of an increase of 15±5 b.p.m. after the administration of the first and second bolus of flumazenil in the 2 patients who required the use of sedation.

The systolic blood pressure values of the patients also underwent no significant changes that would reflect suffering on the part of the patient With an initial value of 110±10 mm Hg, throughout the administration of flumazenil, there was a decrease of 10±5 mm Hg in these values in the 3 cases.

The diastolic blood pressure values of the patients, 75±5 mm Hg at the beginning, developed the same as the former values, with a slightly more pronounced decline (15±5 mm Hg).

Results after the Second Administration of Flumazenil

The withdrawal symptomatology of the patients revealed, as with the first administration, that it was not possible to find a single physical symptom in any of the patients, with the 3 stating that "ideas" and "memories" associated with the drug had a markedly lower intensity.

The heart rate values of the patients (65±5 b.p.m.) remained stable throughout the entire administration of flumazenil, with no elevated peaks at any time.

The systolic blood pressure values of the patients also underwent no significant changes, with values virtually identical to those of the first administration: with an initial value of 115±5 mm Hg, throughout the administration of flumazenil, there was in the 3 cases a decrease of 10±5 mm Hg in these values.

The diastolic blood pressure values of the patients, 75±5 mm Hg at the beginning, developed the same as the former values, again with a slightly more pronounced decline (15±5 mm Hg).

The psychophysiological functions such as appetite and sleep came back very rapidly during hospitalization, progressively from the first night and were virtually normal at the time of discharge.

The second day of hospitalization, the patients were permitted to spend a few hours outside the clinic during the afternoon.

Probably, the most striking result is the spontaneous report from the majority of the patients concerning the absence of anxiety and of the desire to use cocaine.

The invention claimed is:

1. A method for treating cocaine dependency, comprising adminstering therapeutically effective amount of flumazenil to a human patient in need of such treatment, wherein the amount is effective to treat cocaine dependency.

2. The method of claim 1, wherein the flumazenil is administered at time intervals of between about one and about fifteen minutes.

3. The method of claim 1, wherein the flumazenil is administered in quantities between about 0.1 and about 0.3 mg.

4. The method of claim 1, wherein the flumazenil is administered at time intervals of between about one and about fifteen minutes in quantities between about 0.1 and about 0.3 mg.

5. The method of claim 1, wherein the effective amount of flumazenil is between about 1.5 and about 2.5 mg/day.

6. The method of claim 1, wherein about 0.2 mg of flumazenil is administered sequentially at intervals of about 3 minutes.

7. The method of claim 1, wherein the flumazenil is administered orally or parenterally.

8. The method of claim 7, wherein the parenteral administration of flumazenil is intravenous administration.

9. The method of claim 1, wherein the flumazenil is administered before, during or after treatment with an additional agent.

10. The method of claim 9, wherein the additional agent is clomethiazole.

11. The method of claim 9, wherein the additional agent is selected from the group consisting of Vitamin B Complex, Piracetam, vitamins, minerals, proteins, amino acids, disulfiram, fluoxetine, and combinations thereof.

12. The method of claim 1, wherein the flumazenil is administered under sedation.

13. The method of claim 1, wherein the administration of flumazenil reduces the desire to use cocaine.

14. A method for treating cocaine dependency, comprising administering a therapeutically effective amount of flumazenil to a human patient in need of such treatment, wherein the flumazenil is administered at time intervals of between about one and about fifteen minutes in quantities between about 0.1 and about 0.3 mg, wherein the amount is effective to treat cocaine dependency.

15. The method of claim 14, wherein the effective amount of fiumazenil is between about 1.5 and about 2.5 mg/day.

16. The method of claim 14, wherein the administration of flumazenil reduces the desire to use cocaine.

17. The method of claim 1 wherein the therapeutically effective amount of flumazenil is about 2 mg/day.

18. The method of claim 14 wherein the therapeutically effective amount of flumazenil is about 2 mg/day.

* * * * *

UNITED STATES PATENT AND TRADEMARK OFFICE
CERTIFICATE OF CORRECTION

PATENT NO.          : 7,186,711 B2
APPLICATION NO.  : 10/622068
DATED                   : March 6, 2007
INVENTOR(S)        : Juan Jose Legarda Ibañez It is certified that error appears in the above-identified patent and that said Letters Patent is hereby corrected as shown below:

Title Page, item [30]

Insert under "Domestic Priority data"
  This application is a CON of PCT/ESO2/00061 filed 02/08/2002

Title Page, item [56] 2$^{nd}$ Col.

Insert under "Foreign Applications"

SPAIN P 200100342 filed 02/15/2001

Column 1, line 21

Insert a period following the word "attack"

Column 5, line 67

Insert a period following the word "patient"

Claim 1, second line

Delete "administering therapeutically" and insert in place thereof
  --administering a therapeutically--

Claim 15, second line

Delete "fiumazenil" and insert in place thereof --flumazenil--

Signed and Sealed this

Twenty-ninth Day of May, 2007

JON W. DUDAS
*Director of the United States Patent and Trademark Office*